US007246459B2

(12) United States Patent
Lewis

(10) Patent No.: US 7,246,459 B2
(45) Date of Patent: Jul. 24, 2007

(54) SERVICE HANG TAG

(75) Inventor: Mark W. Lewis, Greenville, SC (US)

(73) Assignee: Marjen, Inc., Greenville, SC (US)

( * ) Notice: Subject to any disclaimer, the term of this patent is extended or adjusted under 35 U.S.C. 154(b) by 223 days.

(21) Appl. No.: 11/076,351

(22) Filed: Mar. 9, 2005

(65) Prior Publication Data

US 2006/0213103 A1 Sep. 28, 2006

(51) Int. Cl.

| | |
|---|---|
| ***G09F 3/10*** | (2006.01) |
| ***G09F 3/14*** | (2006.01) |
| ***G09F 3/02*** | (2006.01) |
| ***A61B 5/117*** | (2006.01) |
| ***B42D 15/00*** | (2006.01) |
| ***G09C 3/00*** | (2006.01) |
| ***A45C 11/32*** | (2006.01) |
| ***A45C 11/00*** | (2006.01) |

(52) U.S. Cl. ........................... 40/673; 40/674; 40/675; 40/633; 40/638; 40/665; 40/299.01; 40/27; 283/70; 283/100; 283/103; 283/81; 283/80; 206/38.1; 206/37; 206/37.6

(58) Field of Classification Search ................. 40/674, 40/6, 673, 299.01, 300, 665, 330, 633, 634, 40/668, 669; 24/16 PB; 229/74; 206/38.1; 283/83, 81; D20/27

See application file for complete search history.

(56) References Cited

U.S. PATENT DOCUMENTS

| | | | | |
|---|---|---|---|---|
| 2,578,548 | A * | 12/1951 | Histed | 40/665 |
| 3,318,354 | A * | 5/1967 | Borisof | 206/38.1 |
| 4,726,131 | A * | 2/1988 | Cass | 40/638 |
| 4,846,501 | A | 7/1989 | Del Grande | 282/9 R |
| 4,907,359 | A | 3/1990 | Berman | 40/299 |
| 4,978,144 | A * | 12/1990 | Schmidt et al. | 283/70 |
| 5,782,497 | A | 7/1998 | Casagrande | 283/110 |
| 6,352,287 | B2 | 3/2002 | Casagrande | 283/81 |
| 6,352,608 | B1 | 3/2002 | Garden | 156/249 |
| 6,898,880 | B2 * | 5/2005 | Best et al. | 40/299.01 |
| 7,047,682 | B2 * | 5/2006 | Riley | 40/633 |
| 2004/0074116 | A1 * | 4/2004 | Valenti, Jr. | 40/27 |

* cited by examiner

*Primary Examiner*—Lesley D. Morris
*Assistant Examiner*—Syed A Islam
(74) *Attorney, Agent, or Firm*—Charles L. Schwab; Nexsen Pruet, LLC

(57) ABSTRACT

A vehicle locator and service hang card for vehicle parking and servicing establishments includes an upper portion with a tag number and space for entering customer information and a lower portion made of synthetic paper which an ignition key tag is die cut. The key tag retains its strength when wet. The lower portion may be attached to the upper portion by an adhesive tape.

6 Claims, 2 Drawing Sheets

SERVICE HANG TAG

CROSS REFERENCE TO RELATED APPLICATION

Reference is made to the inventor's co-pending U.S. patent application Ser. No. 10/860,459 filed Jun. 3, 2004 for a Vehicle Locator and Identification Card and Ser. No. 11/007,509 filed Dec. 8, 2004 for a Vehicle Locator and Identification Card.

BACKGROUND OF THE INVENTION

Businesses concerned with parking or servicing vehicles have a problem of correlating the ignition key and the vehicle owner with a particular vehicle. Paper cards with three segments separated by perforations and carrying the same number have been provided so that one segment serves as a claim check, a second segment is placed in the vehicle and a third segment has a key ring stapled to it. A computer type multiple copy form with perforated tear-off strips has been proposed for correlation of ignition key, vehicle and customer which includes perforation lines permitting separation of the form into sections—one to be placed on the vehicle, one to be connected to the ignition key in some undisclosed manner and one to be given to the automobile owner as a claim check. It has been found that in inclement weather, a paper vehicle key tag can become wet; causing it to lose strength, thereby increasing the risk of it breaking and a consequential loss of the key.

BRIEF DESCRIPTION OF THE INVENTION

The upper two segments of a three part automotive vehicle locator and service hang tag or card are formed from a thick sheet of pliable paperboard material and the lower segment includes a vehicle key tag portion made of synthetic paper, which retains its strength when wet. A matching identification number is printed on the three segments of the card. The three segments are established by perforations or slits which permit the segments to be easily separated from one another. A large upper segment of the card includes a punched out hole and a slit from an edge of the card to the hole which permits the upper segment to be attached to the rear view mirror bracket of the vehicle. A second segment of the card is a customer's claim check. A third segment of the card includes a synthetic paper portion in which a removable arrow shaped key tag is defined by long cuts and short connectors which permit easy manual separation of the key tag. Upon removal of the key tag, the head of the arrow is inserted into a T-shaped slot in the tail of the arrow to form a ring for holding an ignition key. The synthetic paper of which the key tag is formed does not lose its strength upon becoming wet, thereby greatly reducing the risk of loss of the key.

BRIEF DESCRIPTION OF THE DRAWINGS

An embodiment of the invention is shown in the accompanying drawings in which.

DETAILED DESCRIPTION OF THE INVENTION

Figure 1:
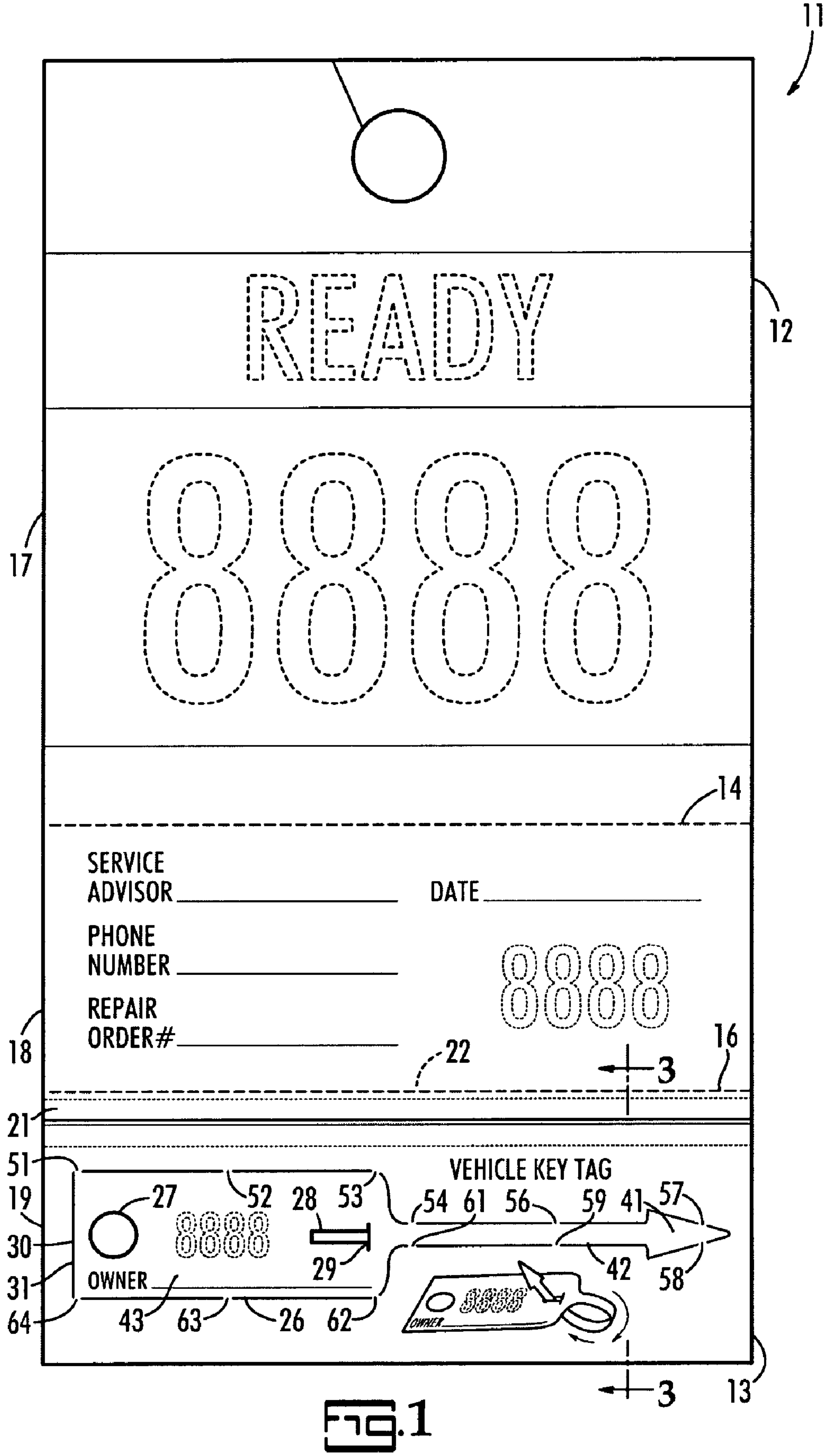
FIG. 1 shows the front of a vehicle locator and identification card.

The automotive vehicle locator and service card or hang tag 11 shown in FIG. 1 includes a relatively thick pliable paperboard sheet 12, forming an upper portion, and a lower portion 13 made of synthetic paper. The paperboard sheet 12 is perforated by cuts, or die cut substantially through its thickness, along lines 14, 16 thereby defining and permitting easy separation of three segments 17, 18, 19 of the card 11. The upper segment 17 is attached to the vehicle. The intermediate segment 18 is the customer's claim check with customer satisfaction questions on its back side. The lower segment 19 includes a relatively narrow bottom part 21 of the paperboard sheet 12 and the lower portion 13 made of synthetic paper, such as 5 SPW Spectralite synthetic paper made by Multi-Plastics, Inc. of Lewis Center, Ohio, USA. 5 SPW Spectralite synthetic paper is a polypropylene film reinforced with other fillers to enhance the white, opaque surface.

Figure 3:
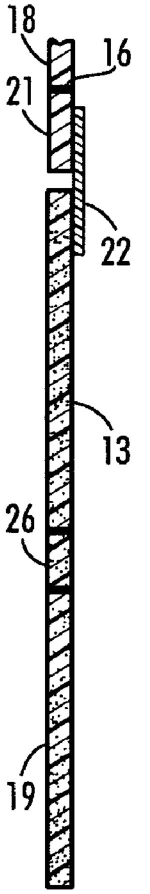
FIG. 3 is an enlarged section taken on line 3-3 in FIG. 1.
Figure 2:
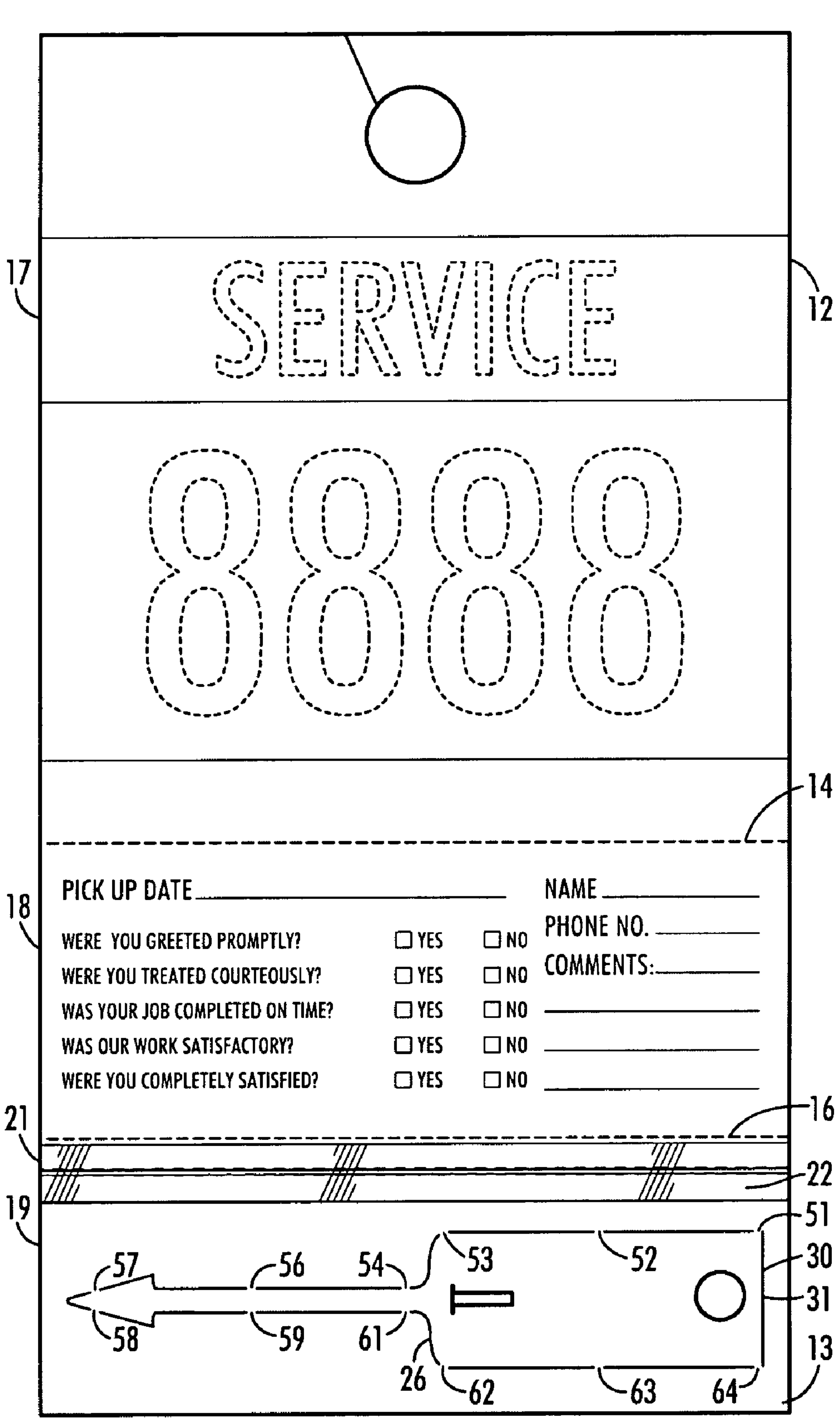
FIG. 2 shows the rear of the card shown in FIG. 1.

As shown in FIGS. 1, 2 and 3, the synthetic paper portion 13 is secured to the part 21 of the paperboard sheet 12 in an end to end relationship by an adhesive tape 22. An elongated arrow shaped vehicle key tag 26 is formed in the portion 31 by long cuts separated by 12 short uncut bridging connectors 51, 52 which are not greater than one thirty second of an inch in length. A die cut 31 forms a blunt tail or rear end of the arrow shaped key tag 26 forming a slot access its width, which provides a convenient slot for insertion of a finger or thumb nail to lift and remove the key tag 26 from the portion 13. The key tag 26 has a head 41, a shank 42 and a tail 43. An opening 27 and a T shaped slot consisting of a narrow channel 28 extending parallel to the shank 42 and a slit 29 at one end of the channel 28 are also die cut in the tag 26. The slit 29 is transverse to the channel 28 and extends laterally beyond the channel 28 in laterally opposite directions. The slit 29 is as long as the width of the shank 42 of the key tag 26 and the head 41 of the key tag 26 is wider than the length of the slit 29. After removal of the key tag 26, an ignition key is placed on the shank 42 of the key tag 26, the head 41 is passed through the channel 28 and the shank 42 is pulled into the slit 29. By forming the key tag 26 of synthetic paper, the key tag 26 resists tearing and is not adversely affected by moisture.

The vehicle locator card 11 with its three segments 17, 18, 19 carrying the same identification indicia and easily separated into segments for placement in the vehicle, for a claim check and for a key tag, helps parking and servicing establishments provide prompt and accurate customer service. By using of synthetic paper for the lower portion 13, the key tag 28 does not lose strength when it becomes wet. Forming the key tag 26 by a plurality of long die cuts with narrow connector between cuts permit the key tag 26 to be easily removed manually from the synthetic portion 13.

What is claimed is:

1. A service hang card, comprising: a thin flat rectangular sheet of material elongated in a top to bottom direction having an upper portion adapted for attachment to a vehicle, said upper portion carrying an identification number and a place for entering customer identification and between said a lower portion including elongated cuts therethough and narrow connectors cuts forming an a removable elongated arrow shaped key tag, at least said lower portion being formed of synthetic paper made of polypropylene film reinforced with fillers, and wherein said arrow shaped key tag has a blunt tail end formed by a single cut which facilitates manual removal of said key tag from said lower portion by a finger or thumb nail.

2. The service hang card of claim 1 wherein said arrow shaped key tag includes a arrow shaped head, a shank and a tail having a T-shaped slot formed by a channel parallel to said shank and a slit at the end of said channel nearest to said head for receiving said shank when said head is inserted through said channel.

3. A service hang card, comprising:

an upper portion adapted for connection to a vehicle, said upper portion being formed of a sheet of paperboard, a lower portion formed of synthetic paper made of polypropylene film with fillers, said lower portions including perforations in said synthetic paper forming a removable elongated arrow shaped key tag, including a cut transverse to the direction of elongation of said key tag defining a blunt end of said key tag, and a tape securing said lower portion to said upper portion in an end to end relationship.

4. The service hang card of claim 3 wherein said arrow shaped key tag includes an arrow shaped head, a shank and a tail having a T-shaped slot formed by a channel parallel to said shank and a slit at the end of said channel nearest to said head for receiving said shank when said head is inserted through said channel.

5. The service hang card of claim 4 wherein said channel is narrower than the width of said shank.

6. A service hang card, comprising: an upper portion adapted for connection to a vehicle and being formed of a sheet of paperboard, and a lower portion formed of synthetic paper made of polypropylene film reinforced with fillers and including cuts forming an a removable elongated arrow shaped key tag, said lower portion being attached to and in coplanar side by side relation with said upper portion and said cuts forming said key tag facilitating manual removal of said key tag from said lower portion, and having a cut in said lower portion forming a blunt end of said arrow shaped key tag transverse to its width facilitating removal of said key tag by a finger or thumb nail.

* * * * *